United States Patent [19]

Hagemann

[11] Patent Number: 4,593,847

[45] Date of Patent: Jun. 10, 1986

[54] BYPASS CLINCHER FOR STITCHING MACHINE

[75] Inventor: Casper W. Hagemann, Racine, Wis.

[73] Assignee: Interlake, Inc., Oak Brook, Ill.

[21] Appl. No.: 729,422

[22] Filed: May 1, 1985

[51] Int. Cl.[4] .............................................. B25C 7/00
[52] U.S. Cl. .................................................... 227/155
[58] Field of Search ................. 227/84, 154, 155, 156, 227/19, DIG. 1

[56] References Cited

U.S. PATENT DOCUMENTS

| | | | |
|---|---|---|---|
| 970,461 | 9/1910 | Briggs | 227/155 X |
| 1,252,011 | 1/1918 | Maynard | 227/155 X |
| 1,956,174 | 4/1934 | Maynard | 227/155 |
| 2,267,185 | 12/1941 | Bauwens | 227/155 X |
| 3,520,462 | 7/1940 | Neeley | 227/155 X |

FOREIGN PATENT DOCUMENTS

| | | | |
|---|---|---|---|
| WO83/00614 | 3/1983 | PCT Int'l Appl. | 227/155 |
| 1339394 | 12/1973 | United Kingdom | 227/155 |

OTHER PUBLICATIONS

Interlake Instruction Manual for Single and Multiple Head Champion Stitchers, Form 1132 R5-80, 1980.

*Primary Examiner*—Paul A. Bell
*Attorney, Agent, or Firm*—Emrich & Dithmar

[57] ABSTRACT

Bypass clinching means for a stitching machine which drives a generally U-shaped staple through associated work, includes a housing pivotally mounting a pair of clinching members which are inclined with respect to the plane of the staple bight portion, the housing defining voids respectively adjacent to the clinching members to receive the excess leg lengths during clinching. A separator plate is disposed between the clinching members and prevents a staple leg from entering the void for the opposite clinching member during the clinching operation. Guide surfaces on the housing and separator plate guide the staple legs to the clinching members.

17 Claims, 9 Drawing Figures

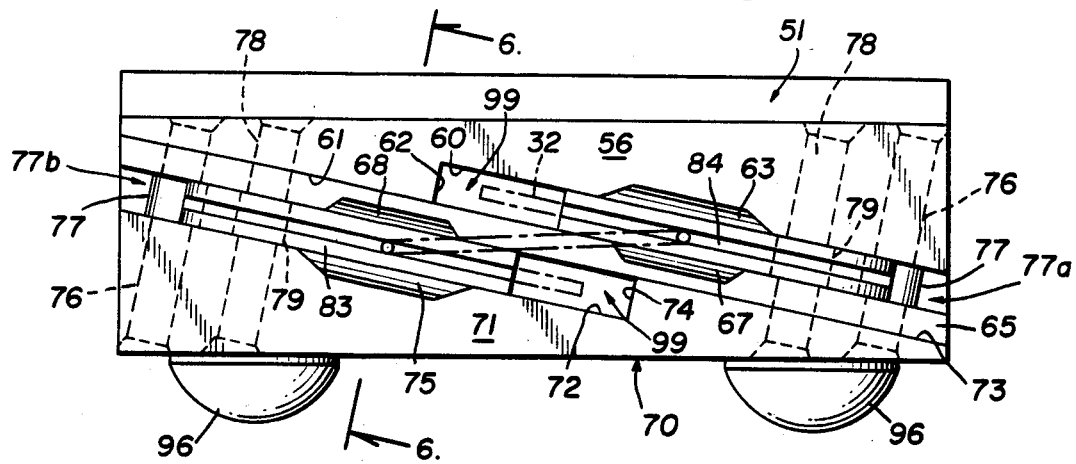
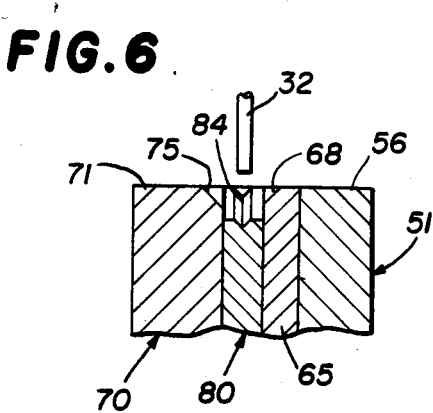
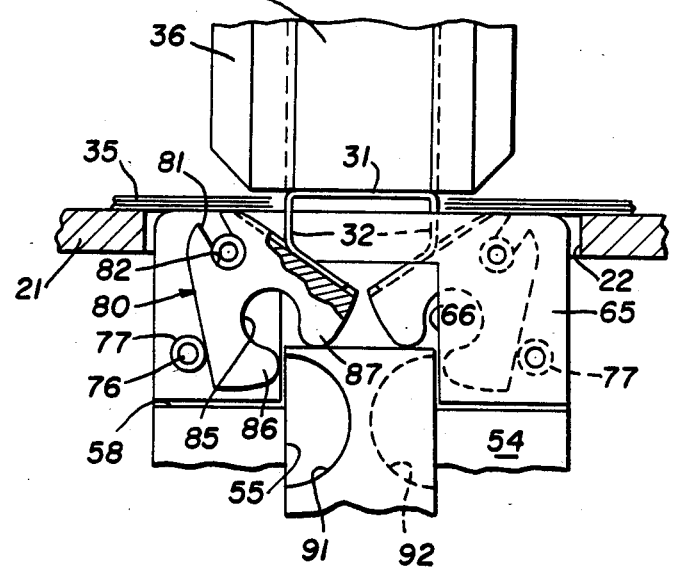
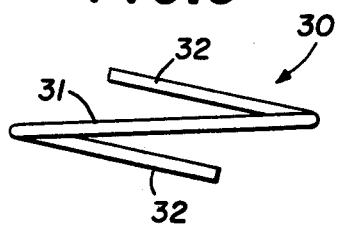
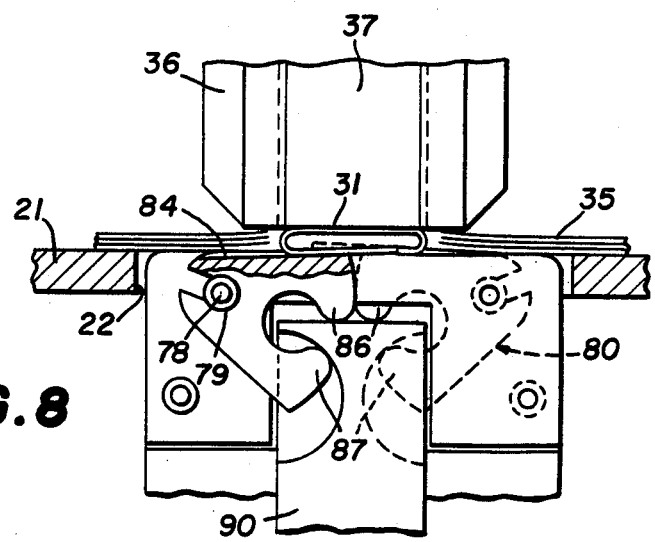

BYPASS CLINCHER FOR STITCHING MACHINE

BACKGROUND OF THE INVENTION

The present invention relates to stitching or stapling machines of the type which drive the legs of a generally U-shaped staple through an associated workpiece and against a clinching mechanism, which folds the legs up against the exit side of the workpiece. In particular, the present invention relates to the clinching mechanism for such a stitching or stapling machine.

This invention is an improvement of the wire stitching machine sold by Interlake, Inc., the assignee of the present invention, under the trademark "CHAMPION STITCHER". That prior stitching machine, which is in turn an improvement of the machine described in U.S. Pat. No. 1,252,011, includes a stitching head having a wire feed mechanism for feeding a predetermined length of wire from the continuous wire supply to a wire holder, where the length of wire is severed from the supply, and a staple-forming and driving mechanism which forms the severed length of wire into a staple and drives it into an associated workpiece. While the invention is designed particularly for use with that prior type of continuous wire stitching head, the principles of the present invention also have application to stitching machines of the type which drive preformed staples which may be fed, for example, from a magazine containing a supply of such staples.

One common type of clinching mechanism used with either the continuous wire or pre-formed staple type of stitching machine, is an in-line arrangement wherein the staple legs in their clinched condition are substantially coplanar with the bight portion of the staple. This arrangement is satisfactory where the workpiece thickness is fixed. But when the thickness of the workpiece can vary over a fairly wide range, the in-line arrangement will result in the staple legs interfering with each other when very thin work is being stapled. This problem can be avoided in the continuous wire stitching machines by adjusting them to vary the length of the staple cut from the continuous wire. But this adjustment is not a simple one, and is suitable only for applications involving fairly long runs at a given thickness and is inconvenient where frequent thickness changes are required.

For this latter condition, a different type of clinching arrangement known as bypass clinching is utilized, wherein the staple legs in their clinched condition are inclined with respect to the plane of the bight portion of the staple and are arranged to overlap or "bypass" each other. The length of the overlap varies as the workpiece thickness varies and, because the staple legs are not in line, they cannot interfere with each other in the clinched condition.

Prior bypass clinchers have utilized a pair of aligned clincher members, each having an angled groove or channel to respectively receive and guide the staple legs. These clincher members have recesses formed on their facing surfaces to accommodate the overlapping portion of the other staple leg. On occasion, particularly when thicker work is being stapled, the staple legs can sometimes stray or wander so that the point of exit from the work will not be in alignment with the point of entry. This can cause the leg to stray into the recessed portion of the associated clincher member, with the result that the leg will not be clinched and will remain in a vertical position.

SUMMARY OF THE INVENTION

It is a general object of the present invention to provide a stitching machine including an improved clinching apparatus, which avoids the disadvantages of prior clinchers while affording additional structural and operating advantages.

An important object of the invention is the provision of a stitching machine clinching apparatus which provides a bypass clinch while effectively preventing interference of the staple legs with each other.

Another object of the invention is the provision of a stitching machine clinching apparatus which ensures proper clinching of each staple.

In connection with the foregoing object, it is another object of the invention is the provision of a clinching apparatus of the type set forth, which is of a simple and economic construction.

These and other objects of the invention are attained by providing in a stitching machine for driving through associated work a U-shaped staple having a pair of dependent legs interconnected by a bight portion disposed parallel to a first plane, and including clinching means having a deflection channel therein disposed parallel to a second plane which is non-parallel to the first plane, wherein the clinching means is movable between a retracted position for receiving the staple legs as they exit the work and deflecting them along the channel, and a clinching position for folding the legs against the work to a clinched condition wherein the legs are disposed in overlapping parallel relationship with each other but are non-parallel with the bight portion, the improvement comprising: means mounting the clinching means for movement parallel to the second plane between the retracted and clinching positions thereof.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 5 is a further enlarged top plan view, similar to FIG. 3, illustrating the clinching mechanism of FIG. 4, and showing the position of the clinched staple in phantom;

FIG. 6 is a fragmentary view in vertical section taken along the line 6—6 in FIG. 5, illustrating a staple leg as it exits the work;

FIG. 7 is an enlarged fragmentary view in partial section of the clinching mechanism of FIG. 2, with the staple shown driven through the work and the clinching mechanism still in its retracted configuration;

FIG. 8 is a view similar to FIG. 7, illustrating the clinching mechanism in its clinching configuration; and FIG. 9 is an enlarged top plan view of the staple of FIG. 8 after it has been clinched.

DESCRIPTION OF THE PREFERRED EMBODIMENT

Figure 1:
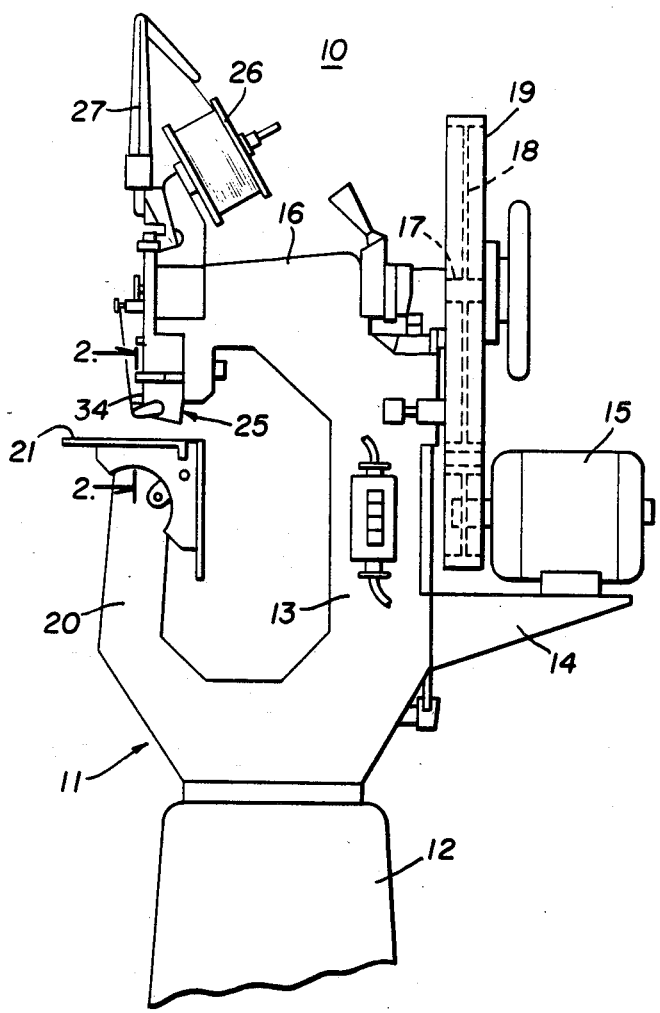
FIG. 1 is a fragmentary, side elevational view of a stitching machine incorporating a clinching mechanism constructed in accordance with and embodying the features of the present invention.

In FIG. 1 there is illustrated a wire stitching machine, generally designated by the numeral 10, which is generally of the type disclosed in the aforementioned U.S. Pat. No. 1,252,011, and includes a stitching head 25 which is also generally of the type disclosed in the '011 patent. The stitching machine 10 includes a frame 11 supported on a suitable pedestal 12 and including an upstanding support post 13. Fixedly secured to the rear end of the support post 13 is a platform 14 supporting thereon an electric drive motor 15. Integral with the support post 13 at the upper end thereof and projecting forwardly therefrom is a generally horizontal support arm 16 which houses a drive shaft 17, the rear end of which is connected to a flywheel 18, which is coupled by a drive belt 19 to the output shaft of the drive motor 15. At the forward end of the drive shaft 17 is linkage (not shown) for converting the rotary motion of the shaft to a vertically reciprocating motion, which is then transmitted to the stitching head 25, which is fixedly secured to the front end of the support arm 16.

The frame 11 also includes an upstanding clincher post 20 disposed forwardly of the support post 13 and provided at the upper end thereof with a pivotally mounted clincher table 21, spaced a predetermined short distance below the bottom of the stitching head 25. The clincher table 21 has an opening 22 therein centrally thereof (see FIG. 2) for providing access to a clincher mechanism 50, which will be explained in greater detail below. Carried by the support arm 16 adjacent to the front end thereof is a supply roll 26 of stitching wire 27 which is fed along a wire guide to the stitching head 25 in a known manner. The machine 10 may be provided with suitable control means for controlling the operation thereof.

The stitching head 25 is very similar in construction to the stitching head disclosed in the aforementioned U.S. Pat. No. 1,252,011, and that used in the Interlake "CHAMPION STITCHER". Accordingly, only so much of the stitching head 25 as is necessary to an understanding of the operation of the present invention will be described herein in detail and the aforementioned patent may be referred to for a more specific explanation of the construction and operation of the remainder of the stitching head 25.

Figure 2:
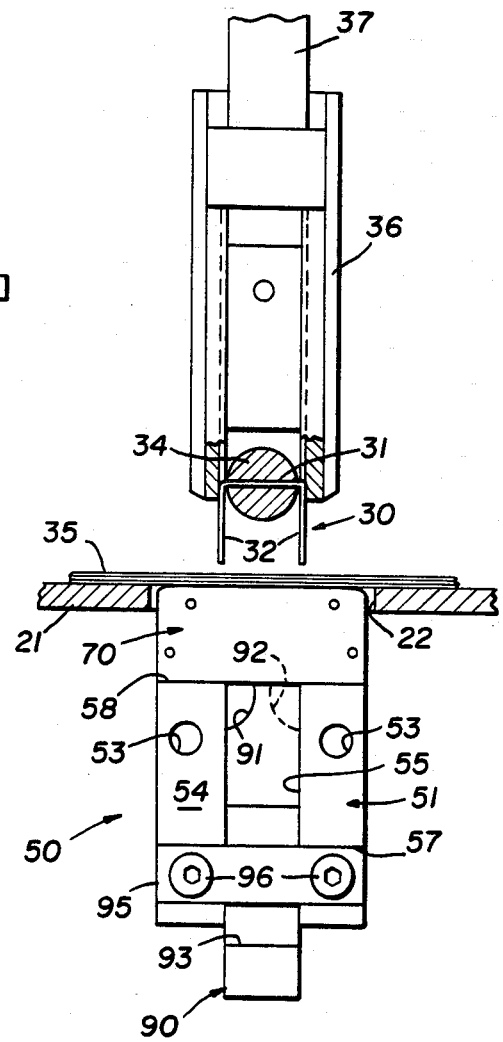
FIG. 2 is an enlarged, fragmentary view in vertical section taken generally along the line 2—2 in FIG. 1, and illustrating the clinching mechanism of the present invention, with the mechanism shown in its retracted configuration before the staple has been driven through the work.
Figure 4:
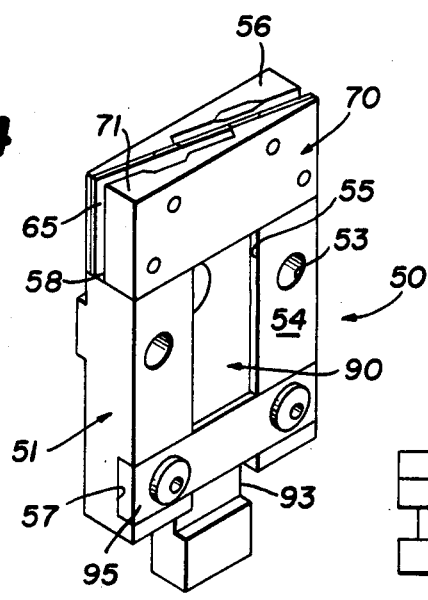
FIG. 4 is a perspective view of the clinching mechanism of FIG. 2, illustrated in its retracted configuration.

Fundamentally, referring also to FIG. 2, the stitching head 25 operates to feed and cut a predetermined length of the stitching wire 27 and form it into a staple 30, generally in the shape of an inverted U, having a bight portion 31 and a pair of depending legs 32. In this regard, the wire 27 is fed vertically downwardly through wire holder 34 and severed, whereupon the wire holder 34 is rotated 90° to bring the cut wire to a horizontal position. A drive slide 36 then passes down over the wire holder 34, picking up the ends of the cut wire 27 and forming it into the staple 30. A drive bar 37 then slides down within the drive slide 36, engages the bight portion 31 of the staple 30, and drives the legs 32 downwardly through associated work 35 which is supported on the upper surface of the clincher table 21. The drive slide 36 is positioned over the opening 22 in the clincher table 21, so that the staple legs 32 pass through the opening 22 to the clinching mechanism 50 which is disposed against the underside of the work 35. The clinching mechanism 50 operates to fold the staple legs 32 upwardly against the underside of the work 35 to complete the stapling operation, all in a conventional manner.

Figure 3:
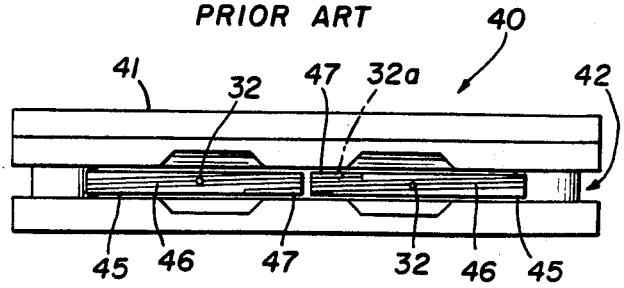
FIG. 3 is a top plan view of a prior art clinching mechanism.

Referring to FIG. 3, there is illustrated a conventional, prior art bypass clinching mechanism 40 which includes a housing 41 forming therein a rectangular channel 42 in which are pivotally mounted a pair of clincher members 45, which are arranged in lateral alignment with each other for pivoting movement about parallel axes. Each of the clincher members 45 has formed in the upper edge thereof an elongated deflection groove 46 which is inclined at an angle to the plane of the bight portion 31 of the staple 30, so that the two deflection grooves 46 are slightly offset from and parallel to each other. Respectively formed in the facing ends of the clincher members 45 are two recesses or voids 47 which are respectively aligned with the deflection grooves 46 of the opposite clincher members 45.

In normal operation, the staple legs 32 exit the work 35 and enter the deflection grooves 46, being angled downwardly and inwardly therealong. The clincher members 45 then pivot upwardly to fold the legs 32 against the work 35 and complete the clinching operation. The distal ends of the folded legs normally extend beyond the ends of the associated deflection grooves 46, the recesses 47 being provided to accommodate these projecting ends of the staple legs 32.

A difficulty with the prior art bypass clinching mechanism 40 is that occasionally the staple legs 32 will drift from the in-line vertical position as they pass through the work 35. This is particularly true when thick work is being stapled. Thus, the point at which a leg 32 exits the work 35 may not be in vertical alignment with the entry point. Frequently, the misalignment is sufficiently large that the leg 32, on exiting the work 35, completely misses the deflection groove 46 and enters the recess 47, as indicated by the position 32a in FIG. 3. When this happens, the leg 32 does not get clinched at all, and remains projecting straight down from the work 35.

Referring now also to FIGS. 4–8, there is illustrated the bypass clinching mechanism 50 in accordance with the present invention, which avoids these disadvantages of prior bypass clinching mechanisms. The clinching mechanism 50 includes a rectangular back plate 51, having a pair of bores 53 therethrough for accommodating associated fasteners (not shown), securely to mount the clinching mechanism 50 to the clincher post 20. The back plate 51 has a flat, planar front surface 54 in which is formed a rectangular vertical channel 55 (FIG. 2), which extends the entire vertical length of the back plate 51 to a top surface 56 thereof. A horizontal channel 57 is also formed in the front surface 54 adjacent to the lower end thereof, intersecting the vertical channel 55 but having a depth less than that of the vertical channel 55.

The front surface 54 is recessed or cut away at the upper end thereof to form a ledge 58 spaced below the top surface 56 and substantially parallel thereto. Extending vertically between the ledge 58 and the top surface 56 are a flat slide surface 60 (FIG. 5) and a flat bearing surface 61 which are offset from each other and interconnected by a perpendicular shoulder or step 62. The surfaces 60 and 61 are substantially parallel to each other and are inclined at a predetermined acute angle with respect to the front surface 54 of the back plate 51, so that the top surface 56 is generally pie or wedge shaped. Formed in the top surface 56 is a downwardly and forwardly beveled guide surface 63 which intersects the vertical slide surface 60.

Disposed against the bearing surface 61 in back-to-back engagement therewith is a flat rectangular separator plate 65, which is dimensioned to rest upon the ledge 58 with its top edge substantially flush with the top surface 56, and with its side edges respectively substantially flush with the opposite sides of the back plate 51. Formed in the bottom edge of the separator plate 65 centrally thereof is a rectangular notch 66 (FIG. 7) which is substantially aligned with the vertical channel 55 in the back plate 51. The upper edge of the separator plate 65 has two beveled guide surfaces 67 and 68 formed therein, which respectively slope downwardly toward the rear and front surfaces of the separator plate 65.

The clinching mechanism 50 also includes a rectangular front plate 70 which also sits on the ledge 58 and has a top surface 71 substantially coplanar with the top surface 56 of the back plate 51. Formed on the rear of the front plate 70 are a flat planar slide surface 72 (FIG. 5) and a flat planar bearing surface 73. The surfaces 72 and 73 are offset from each other and interconnected by a perpendicular shoulder or step 74, the surfaces 72 and 73 being parallel to each other and to the inclined surfaces 60 and 61 of the back plate 51. Formed in the top surface 71 is a beveled guide surface 75 which is inclined downwardly and rearwardly to the slide surface 72.

In use, the front plate 70 is disposed with the bearing surface 73 thereof disposed in back-to-back engagement with the front surface of the separate plate 65. A pair of pins, such as rivets 76, extend through complementary openings in the back plate 51, the separator plate 65 and the front plate 70 for holding the parts together in an assembled condition. Each of the pins 76 has an enlarged-diameter spacer portion 77, which cooperates with the shoulders 62 and 74 for maintaining predetermined separations between the separator plate 65 and the slide surfaces 60 and 72, respectively. In this assembled condition, the beveled guide surfaces 63 and 67 are disposed in facing relationship with each other, and the beveled guide surfaces 68 and 75 are disposed in facing relationship with each other. The axes of the pins 76 are parallel to each other and substantially perpendicular to the separator plate 65. The rear surface of the separator plate 65 and the opposite slide surface 60 cooperate with the step or shoulder 62 to define a first pocket or compartment 77a, while the front surface of the separator plate 65 cooperates with the opposed slide surface 72 and the step or shoulder 74 to define a second rectangular pocket or compartment 77b.

Also extending through complementary openings in the back plate 51, the separator plate 65 and the front plate 70 are a pair of pivot pins, such as rivets 78, each having an enlarged-diameter bearing portion 79 respectively disposed in the pockets or compartments 77a and 77b. Respectively pivotally mounted on the pivot pins 78 are a pair of clincher members 80, which are respectively disposed in the compartments 77a and 77b for pivotal movement between retracted positions, illustrated in FIG. 7, and clinching positions, illustrated in FIG. 8. The clincher members 80 are identically constructed, so that only one will be described in detail.

Each of the clincher members 80 is a generally flat, plate-like member of generally triangular shape having a pivot slot 81 formed in the apex thereof with an enlarged-diameter portion 82 for receiving therein the bearing portion 79 (see FIG. 8) of the associated pivot pin 78. The clincher member 80 has an elongated, flat, upper clinching edge 83 (FIG. 5) which extends longitudinally of the associated pocket 77a or 77b. The clinching edge 83 has formed therein centrally thereof and extending the length thereof a deflection channel 84, which is generally V-shaped in transverse cross section (see FIG. 6). Formed in the base edge of each of the clincher members 80 is an arcuate aperture 85 (FIG. 7) which defines two rounded lobes 86 and 87.

Slidably disposed in the vertical channel 55 of the back plate 51 is an elongated, flat, rectangular slider bar 90, which has two semicircular recesses 91 and 92 formed respectively in the front and rear surfaces thereof adjacent to the upper end thereof. Extending transversely across the front surface of the slider bar 90 adjacent to the lower end thereof is a retaining notch 93. The bottom end of the slider bar 90 is adapted to be coupled to linkage (not shown) disposed in the clincher post 20, which linkage is in turn coupled by suitable means to a clincher drive mechanism for effecting a vertical reciprocating movement of the slider bar 90 in the vertical channel 55. A retaining bar 95 is disposed in the horizontal channel 57, being fixedly secured to the back plate 51 by fasteners 96. The retainer bar 95 is accommodated in the retaining notch 93 for cooperation therewith to hold the slider bar 90 in place in the channel 55 and to limit the vertical travel thereof. It will be noted that the clincher members 80 are shorter than the compartments 77a and 77b and are so positioned therein as to leave at the inner ends thereof voids 99 (FIG. 5).

The upper end of the slider bar 90 bears against the lobes 87 of the clincher members 80 (see FIGS. 7 and 8). When the slider bar 90 is in its lowered position, illustrated in FIGS. 2 and 7, the clinching mechanism 50 is in a retracted configuration, with the lobes 87 of the clincher members 80 resting upon the slider bar 90. When the slider bar 90 is driven upwardly to its raised position, illustrated in FIG. 8, it pivots the clincher member 80 upwardly to a clinching configuration of the clinching mechanism 50. In this configuration, the lobes 87 of the clincher members 80 pivot inwardly, being accommodated in the semicircular recesses 91 and 92 in the slider bar 90.

In operation, when a piece of work 35 is to be stapled, the clinching mechanism 50 is in its retracted configuration, illustrated in FIG. 2. As the drive bar 37 drives the staple 30 through the work, the legs 32 exit the work and respectively enter the deflection channels 84 in the clincher members 80, being deflected downwardly and inwardly therealong, as illustrated in FIG. 7. The driving of the staple 30 is completed when the drive bar 37 bottoms out on the work 35. At this point, the stitching machine 10 operates to drive the slider bar 90 upwardly, pivoting the clincher members 80 upwardly to their clinching positions, illustrated in FIG. 8. This upward movement of the clincher members 80 folds the staple legs 32 upwardly against the bottom surface of the work 35 in a parallel, side-by-side or "bypass" configuration, illustrated in FIGS. 5, 8 and 9. As the legs 32 are folded, depending upon the thickness of the work 35, the distal ends of the legs 32 may slide off the ends of the clincher members 80, being accommodated in the voids 99.

In the event that the staple legs 32 wander slightly off center as they pass through the work 35, the guide surfaces 67 and 63 cooperate to guide the staple leg 32 in to the deflection channel 84 of the clincher member 80 in the compartment 77a. In like manner, the guide surfaces 68 and 75 serve to guide the other staple leg 32 with respect to the clincher member 80 in the compartment 77b. A significant aspect of the invention is that even if the staple leg 32 is slightly off center as it exits the work 35, so as to miss the deflection channel 84 in the clincher member 80, it cannot ride into the void 99 for the other leg 32. First of all, because the compartments 77a and 77b are not aligned with each other, as the staple leg 32 rides off the end of the clincher member 80, it is already nearly past the outer end of the void 99 for the other leg 32, leaving very little space to cross over into that opposite void 99. Furthermore, the separator plate 65 effectively isolates the clincher members 80 from each other, preventing a staple leg 32 from sliding off the side of the clincher member 80 and entering the opposite void 99. This effectively prevents interference of the staple legs 32 with each other and ensures the clinching of both staple legs 32 during each clinching operation.

From the foregoing, it can be seen that there has been provided an improved clinching mechanism which is of simple and economical construction and which effectively ensures a proper clinching of each staple. This is a particularly useful advantage in applications such as the finishing station of a high-speed copying machine where frequent changes in work thickness are encountered, although it will be appreciated that the present invention is useful in other applications as well.

I claim:

1. In a stitching machine for driving through associated work a U-shaped staple having a pair of dependent legs interconnected by a bight portion disposed parallel to a first plane, and including clinching means having a deflection channel therein disposed parallel to a second plane which is non-parallel to the first plane, wherein the clinching means is movable between a retracted position for receiving the staple legs as they exit the work and deflecting them along the channel, and a clinching position for folding the legs against the work to a clinched condition wherein the legs are disposed in overlapping parallel relationship with each other but are non-parallel with the bight portion, the improvement comprising: means mounting said clinching means for movement parallel to the second plane between the retracted and clinching positions thereof.

2. The stitching machine of claim 1, wherein said mounting means includes means mounting said clinching means for pivotal movement between the retracted and clinching positions thereof.

3. The stitching machine of claim 2, wherein said clinching means is pivotally movable about an axis disposed substantially perpendicular to the second plane.

4. The stitching machine of claim 1, wherein said clinching means includes a pair of clinching members respectively engageable with the legs of the staple.

5. The stitching machine of claim 4, wherein said clinching members are spaced apart in a direction perpendicular to the second plane.

6. The stitching machine of claim 5, wherein each of said clinching members has a deflection channel formed therein, both of said deflection channels being disposed parallel to the second plane.

7. The stitching machine of claim 4, and further including guide means for guiding the staple legs respectively to said clinching members.

8. In a stitching machine for driving through associated work a U-shaped staple having a pair of dependent legs interconnected by a bight portion, and a pair of clinching members movable between retracted positions for respectively receiving the staple legs as they exit the work and clinching positions for folding the legs against the work to a clinched condition wherein the legs are disposed in overlapping parallel relationship with each other but are non-parallel with the bight portion, the improvement comprising: separating means disposed between the clinching members for preventing interference between the staple legs during the clinching operation.

9. The stitching machine of claim 8, wherein said separating means comprises a flat plate disposed between the clinching members.

10. The stitching machine of claim 9, wherein said clinching members are mounted for pivotal movement about axes disposed substantially perpendicular to said separating plate.

11. The stitching machine of claim 9, and further including support means carrying the clinching members and said separating plate, said support means cooperating with said separating plate to define two separated compartments respectively accommodating the clinching members.

12. The stitching machine of claim 9, wherein said separating plate is substantially flat and lies in a plane disposed non-parallel to the plane of the staple bight portion.

13. In a stitching machine for driving through associated work a U-shaped staple having a pair of dependent legs interconnected by a bight portion, and a pair of clinching members movable between retracted positions for respectively receiving the staple legs as they exit the work and clinching positions for folding the legs against the work to a clinched condition wherein the legs are disposed in overlapping parallel relationship with each other but are non-parallel with the bight portion, the improvement comprising: a first support member having a first flat planar surface disposed non-parallel to the plane of the bight portion, a second support member having a second flat planar surface, means interconnecting said first and second support members in a support configuration with said first and second surfaces disposed in spaced-apart relation parallel to each other but non-parallel to the plane of the bight portion, a separating plate disposed between said first and second surfaces parallel thereto for cooperation therewith to define two separated compartments, and means mounting the clinching members respectively in said compartments for pivotal movement between the retracted and clinching positions thereof respectively about axes disposed perpendicular to said first and second surfaces.

14. The stitching machine of claim 13, and further including guide means for guiding the staple legs respectively to said clinching members.

15. The stitching machine of claim 14, wherein said guide means includes guide surfaces formed on said separating plate and on each of said first and second support members.

16. The stitching machine of claim 13, wherein each of said first and second support members includes a bearing surface, said bearing surfaces being respectively disposed in engagement with the opposite sides of said separating plate.

17. The stitching machine of claim 16, wherein said bearing surfaces are substantially parallel to said first and second planar surfaces and are offset with respect thereto.

* * * * *